United States Patent [19]

Miale et al.

[11] 4,054,511

[45] Oct. 18, 1977

[54] ACTIVATION OF FERRIERITE AND CONVERSION OF HYDROCARBONS THEREWITH

[75] Inventors: Joseph N. Miale, Trenton; David H. Olson, Pennington, both of N.J.

[73] Assignee: Mobil Oil Corporation, New York, N.Y.

[21] Appl. No.: 707,727

[22] Filed: July 22, 1976

Related U.S. Application Data

[62] Division of Ser. No. 482,286, June 24, 1974, Pat. No. 3,997,474.

[51] Int. Cl.$^2$ .................... C10G 13/02; C01B 29/28; B01J 8/24
[52] U.S. Cl. .................... 208/120; 208/111; 252/441; 252/442; 252/450; 252/455 Z; 252/477 R
[58] Field of Search .................... 208/120, 111; 260/683.68

[56] References Cited

U.S. PATENT DOCUMENTS

| | | | |
|---|---|---|---|
| 3,354,077 | 11/1967 | Hansford | 208/111 |
| 3,375,064 | 3/1968 | Miale et al. | 423/328 |
| 3,375,065 | 3/1968 | McDaniel et al. | 423/275 |
| 3,402,996 | 9/1968 | Maher et al. | 423/328 |
| 3,894,940 | 7/1975 | Scherzer et al. | 208/120 |

*Primary Examiner*—Delbert E. Gantz
*Assistant Examiner*—G. E. Schmitkons
*Attorney, Agent, or Firm*—Charles A. Huggett; Claude E. Setliff

[57] ABSTRACT

Ferrierite ore is activated for normal paraffin conversion by exchanging with the ammonium ion, heating in air at a temperature from about 775° F to about 1000° F and exchanging again with the ammonium ion. Activation of ammonium ferrierite for conversion of branched paraffins is accomplished (1) by treatment with HF or (2) by heating in steam at a temperature within the above range, followed by exchange with ammonium ion. Ferrierite ore per se may be treated with HF, but to complete activation for conversion of branched paraffins, the HF treated ore must be exchanged with the ammonium ion.

8 Claims, No Drawings

ACTIVATION OF FERRIERITE AND CONVERSION OF HYDROCARBONS THEREWITH

CROSS REFERENCE TO RELATED APPLICATIONS

This application is a division of copending application Ser. No. 482,286 filed June 24, 1974 now U.S. Pat. No. 3,997,474.

BACKGROUND OF THE INVENTION

1. Field of the Invention

This invention is concerned with the activation of ferrierite for the catalytic conversion of hydrocarbons. More particularly, it is concerned with methods for activating ferrierite in a way that makes it selective for cracking normal paraffins and controllable amounts of branched paraffins.

2. Discussion of the Prior Art

It is well known in the prior art that certain zeolites including those designated by the Linde Division of Union Carbide Corporation by the letters X,Y, A and L and the naturally occurring crystalline zeolites, chabazite, erionite, faujasite and mordenite, can be treated by steps comprising heating and ion exchange. For example, U.S. Pat. No. 3,402,996 is concerned with a method of cation exchanging these and other zeolites, the method comprising a convetional ion exchange step, a calcination step at 400° to 1500° F and an additional conventional ion exchange step.

U.S. Pat. No. 3,375,065 discloses a method of producing a thermally stable synthetic faujasite containing less than 1% Na$_2$O by (1) exchanging the faujasite with ammonium cations, heating the exchanged product above 350° F, exchanging again with ammonium cations and finally exchanging with magnesium or rare earth or mixtures thereof. Stability of the faujasite is attained by reducing the concentration of the ammonium ion.

In one of its aspects, U.S. Pat. No. 3,354,077 teaches that an ammonium Y crystal-type zeolite can be heated at 300°-700° F in an atmosphere containing water vapor without destruction of crystallinity; stabilization of this zeolite is completed by continuing the heating up to about 1200° F in a water vapor atmosphere.

SUMMARY OF THE INVENTION

In accordance with the present invention a method of producing an active, stable ferrierite is provided, the method comprising contacting the ferrierite with the ammonium ion or HF and a second contact wherein the ammonium ion-treated ferrierite is contacted with the ammonium ion or HF and the HF-treated ferrierite contacted with the ammonium ion, the ammonium ion-treated ferrierite from the first contact being heated in air or steam at from about 775° F to about 1000° F prior to the second contact with the ammonium ion.

DESCRIPTION OF SPECIFIC EMBODIMENTS

Briefly stated, the method of this invention comprises calcining an ammonium ferrierite at from about 775° F to about 1000° F. Following this step, the ferrierite is further ion exchanged with ammonium ions. These exchanges, when coupled with heating in air within a critical temperature range, produce a zeolite that is stable, active and selective for converting the normal paraffins of a hydrocarbon feed stock. By treating the ammonium ferrierite with steam, following this with exchange with ammonium ion or by merely treating the ammonium ferrierite with HF, a catalyst is obtained that is capable of cracking some of the branched paraffins as well as the normal paraffins. Also, if ferrierite, per se, is treated with HF and this is followed by ammonium ion exchange, the catalyst obtained is capable of the same cracking activity.

The zeolite useful in the practice of this invention is natural ferrierite. The naturally occurring ferrierite has been described by Graham (Roy. Soc. Canada, Proc. and Trans., 3rd Ser., 12, 185-190) and by Staples (Am. Mineral, 40 1095-99). The formula of the natural mineral ferrierite is given as (Na, K)$_4$Mg$_2$(Si$_{30}$Al$_6$) O$_{72}$. (OH)$_2$.18H$_2$O. The oxide formula is given in "Zeolite Molecular Sieves", John Wiley and Sons, Inc. (1974) as (Na$_2$, Mg)O.Al$_2$O$_3$.11.1 SiO$_2$.6.5 H$_2$O.

The ferrierite ore employed as starting material in the method of this invention is an ore having from 60–90% ferrierite which has a very low hexane cracking activity ($\alpha < 1$). When it is ion exchanged to its ammonium form and calcined, this material is stable, moderately active ($\alpha \approx 200$) and selective for cracking straight-chain hydrocarbons. These characteristics of ammonium ferrierite are not altered by successive conventional ion exchanges with ammonium salts. However, it has been discovered that if the ammonium ferrierite is air-calcined and reexchanged with ammonium salts, a material is formed which has substantially double the activity for normal hexane cracking (as measured by the $\alpha$-value), but retains its selectivity for cracking normal paraffins. (The alpha test used is a modification of the test defined in "Superactive Crystalline Aluminosilicate Hydrocarbon Catalysis" by P. B. Weisz et al. in the Journal of Catalysis, vol. 4, No. 4, August 1965). If, instead of calcining in air, the ammonium ferrierite is steamed at the requisite temperature, i.e. between about 775° F and about 1000° and then ammonium exchanged, or is treated directly with HF, without heating or further ammonium ion exchange, a catalyst is obtained that, in addition to yielding substantial products from the cracking of normal paraffins, also yields significant products from cracked branched paraffins.

In carrying out the process, natural ferrierite is contacted with an exchange solution of the ammonium salt. The concentration of the salt solution and the particular anion are not critical. Any of the soluble ammonium salts such as, for example, the chloride, sulfate or nitrate as well as the organic salts, such as the acetate or formate, may be employed. The exchange is carried out by contacting the salt solution with the zeolite for a period of time ranging from a few minutes to several months, preferably from 2 to about 20 hours. The rate of exchange can be increased by carrying out the exchange at an elevated temperature. Suitable exchange may be carried out at a temperature of from about 50° F to about 400° F.

Following the exchange, the zeolite is water washed to remove any excess salts. The next step involves heating the ammonium ferrierite in air. As will be shown hereinafter, temperatures of 750° F and below are not adequate for the purposes of the invention. The temperature of calcination in air must be at from about 775° F to about 1000° F.

When steam is employed in place of air, the atmosphere may be from 20% to 100% steam, preferably 100%. Again, the temperature is critical, being within the above appropriate range of 775° F to 1000° F.

The HF employed is in aqueous media containing from about 0.2% by weight of HF up to its solubility limit. We prefer to use those solutions containing from about 0.2 to 50% by weight of HF, preferably from about 0.5 to 25%. The reaction is generally carried out from about 2 minutes to about 10 hours, preferably from about 5 minutes to about 2 hours.

As in the case with many catalysts, it may be desirable to incorporate the completed catalyst with another material resistant to the usual conditions employed in organic conversion processes. Such materials include active and inactive materials and synthethic or naturally occurring zeolites as well as inorganic materials such as clays, silica and/or metal oxides. The latter may be either naturally occurring or in the form of gelatinous precipitates, sols or gels, including mixtures of silica and metal oxides. Frequently, the zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the product from the process of this invention include the montmorillonite and kaolin family, which families include the sub-bentonites, and the kaolins commonly known as Dixie, McNamee, Georgia and Florida clays or others in which the main mineral constituents are halloysite, kaolinite, dickite, nacrite, or anauxite. Such clays can be used in the raw state as originally mined or initially subjected to calcination, acid treatment of chemical modification.

In addition to the foregoing materials, the catalyst can be composited with a porous matrix material such as silica-alumina, silica-magnesia, silica-sirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided activated and inorganic oxide gel matrix may vary widely with the ferrierite content ranging from about 1 to about 90 percent by weight and more usually in the range of about 2 to about 80 percent by weight of the composite.

Having described the invention in a general way, the following examples are offered as specific illustrations of the method. It will be understood that they are illustrative only and are not meant unnecessarily to limit the invention.

EXAMPLE 1

A 300 gram sample of ferrierite ore from Lovelock, Nevada, was crushed to 14+ mesh, then ball-milled to a particle size $<5\mu$. An aliquot was pelleted and resized to 14/30 mesh and tested for hexane cracking activity by the conventional $\alpha$-test. Results as shown in Table I.

EXAMPLE 2

A 167g aliquot of ferrierite powder from Example 1 was refluxed overnight with 2 liters of 4N ammonium nitrate, filtered and washed with boiling water. Ion exchange procedure was then repeated three times. A 14/30 aliquot was tested for hexane-cracking activity by the $\alpha$-test modified by feeding an equimolar mixture of n-hexane, 3-methylpetane, and 2,3-dimethylbutane at 1-LHSV, 20:1 He/$C_6$ ratio (3 seconds contact time). Specifically an equimolar mixture of n-hexane, 2-methylpentane and 2,3-dimethylbutane was pumped into a tee stuffed with glass wool. The hydrocarbon mix was then picked up by a helium stream and carried to the catalyst.

Results as shown below in Table I.

TABLE I

| Ex- ample | Ferrierite form | Test Temperature | n-hexane Conversion | $\alpha$ | $iC_6$ Conversion |
|---|---|---|---|---|---|
| 1 | untreated | 1000° F | 7.6% | 0.6 | ~0 |
| 2 | $NH_4$ | 800° F | 37.9% | 190 | ~0 |

The degree of exchange of Example 2 was checked by TGA ammonia evolution after the second and fourth exchange treatments and found to be the same for both materials.

EXAMPLE 3

An aliquot of ammonium ferrierite from Example 2 was calcined in air for five hours.

EXAMPLE 4

A 4 gram aliquot of ferrierite from Example 3 was ion exchanged with $4M(NH_4)_2SO_4$ overnight, then washed with boiling water. The procedure was repeated and the catalyst dried 1 hour at 110° C.

EXAMPLE 5

An in Example 3 but using 5 hours at 800° F for calcination.

EXAMPLE 6

An aliquot of Example 5 exchanged as described in Example 4.

EXAMPLE 7

The same as Example 3 but using 10 hours air calcination at 1000° F.

EXAMPLE 8

An aliquot of Example 7 treated as described in Example 4.

The products of Examples 2-8 were tested for their effectiveness in the n-hexane cracking test and for their ability to convert isohexane. The example 2, 4, 6 and 8 products were tested for their ability to exchange $NH_3$. Table II shoes this ability.

TABLE II

| Examples | Calcination hrs. at ° F. | | $\alpha$ (800° F) | | Exchangeability[1] Meq. $NH_3$/g | $iC_6$ Conv |
|---|---|---|---|---|---|---|
| | | | Before Exchange | After Exchange | | |
| 2 | | | | 190 | 1.42 | 0 |
| 3 | 5 | 750 | 120 | | | 0 |
| 4 | | | | 120 | 1.33 | 0 |
| 5 | 5 | 800 | 200 | | | 0 |

TABLE II-continued

| Examples | Calcination hrs. at ° F. | | α (800° F) | | Exchangeability[1] Meq. NH$_3$/g | iC$_6$ Conv |
|---|---|---|---|---|---|---|
| | | | Before Exchange | After Exchange | | |
| 6 | | | | 400 | 1.08 | 0 |
| 7 | 10 | 1000 | 210 | | | 0 |
| 8 | | | | 350 | 0.84 | 0 |

[1]The ammonium form of the zeolite is heated in a thermogravimetric apparatus. Precise measurement of NH$_3$ evolved is thus made and calculated as meq./g (milliequivalents of H+ present in 1 gram of zeolite).

The products of examples 2–8 were tested for their ability to crack hexanes. They were found to the completely selective for n-hexane cracking (essentially no cracking of isohexanes was observed). The degree of ammonium exchange was measured on samples exchanged after calcination (examples 2, 4, 6 and 8, and the tests showed that the temperature of intermediate air calcination step appears to be critical. Thus, at the 750° F calcination, the reexchanged did not change activity or selectivity; at the 800° F calcination, the hexane cracking activity was increased from 200 to 400 upon reexchange.

EXAMPLE 9

An aliquot of ammonium ferrierite from Example 2 was steamed (100% steam) for 16 hours at 780° and tested for hexane cracking.

EXAMPLE 10

An aliquot of ferrierite from Example 9 was ion exchanged as in Example 4.

EXAMPLES 11, 12

An aliquot of Example 2 treated as in Examples 9 and 10, but using 855° F as the steaming temperature.

EXAMPLES 13, 14

An aliquot of Examples 2 treated as in Examples 9 and 10 but using 1000° F as the steaming temperature.

EXAMPLES 15, 16

An aliquot of Example 2 treated as in Examples 9 and 10 but using 16 hours at 780° F followed by 16 hours at 1290° F as the steaming conditions.

EXAMPLE 17

An aliquot of Example 16 given two contacts with 0.25M (NH$_4$)$_2$EDTA (pH=7). Results of hexane cracking tests Examples 10–18 are shown in Table III.

EXAMPLE 18

A 4g aliquot of Example 2 ferrierite was slurried in 60 ml hot water (about 100° C) to which was added 0.5 ml of 49.7% aqueous HF. After 15 minutes, a second 0.5 ml portion of 49.7% HF was added. Contact was continued for 45 minutes. The material was then filtered, washed three times with 120 ml hot 1N NH$_4$OH, and dried 1 hour at 110° C prior to testing to determine its ability to convert branched paraffins. Results as shown in Table IV.

TABLE IV

| Example | Treatment | 5-Minute Conversion (800° F) | | | α (800° F) |
|---|---|---|---|---|---|
| | | n-C$_6$ | 3MeC$_5$ | 2,3Me$_2$C$_4$ | |
| 2 | None | 37.9 | 0 | 0 | 190 |
| 18 | Aq. HF | 42.1 | 15.8 | 21.5 | 235 |

This table shows that, like the steamed and reexchanged ferrierite, the HF treated ferrierite converts substantial quantities of isohexanes.

EXAMPLE 19

A sample of erionite ore from Jersey Valley, Nevada was ammonium exchanged. An aliquot of the ammonium erionite was treated with aqueous HF as in example 18. These samples were then tested for hexane cracking as above. Results are shown in Table below.

| NH$_4$ Erionite | Conversion, wt.% | |
|---|---|---|
| | n-Hexane | iso hexanes |
| untreated | 62% | 0 |
| HF-treated | 27% | 0 |

This illustrates that the HF technique is not generally applicable to all small port zeolites. The ammonium erionite retained its selectivity for cracking only normal paraffins and lost much of its activity due to consider-

TABLE III

| Example | Steam Temperature (° F) | α (800° F) | | | Exchangeability (Meq NH$_3$ per gram) | Conversion (% at 800° F) | | |
|---|---|---|---|---|---|---|---|---|
| | | Before Exchange | After Exchange | After EDTA | | nC$_6$ | 3MeC$_5$ | 2,3Me$_2$C$_4$ |
| 2 | None | | 190 | | 1.42 | 35.9 | 0 | 0 |
| 9 | 780 | 130 | | | | | | |
| 10 | 780 | | 210 | | 0.36 | 39.2 | 11 | 25 |
| 11 | 855 | 60 | | | | | | |
| 12 | 855 | | 165 | | 0.36 | 32.2 | 11.5 | 18 |
| 13 | 1000 | 23 | | | | | | |
| 14 | 1000 | | 104 | | 0.27 | 20.9 | 6 | 8 |
| 15 | 780/1290 | 1 | | | | | | |
| 16 | 780/1290 | | 36 | | 0.28 | 8.2 | 1.5 | 3.5 |
| 17 | 780/1290 | | | 43 | | 9.8 | 1.6 | 2.4 |

Note that substantial amounts of isohexanes are converted by ferrierite catalysts which were steamed and then reexchanged. Further steaming about about 1000° F substantially reduces conversion of hexanes.

able structural damage.

We claim:

1. A process for the catalytic conversion of a hydrocarbon charge comprising normal paraffins and isoparaffins, both having from 4 to 20 carbon atoms, which comprises contacting same under hydrocarbon conversion conditions with a catalyst comprising a ferrierite activated by steps comprising a first contact of said ferrierite with the ammonium ion or aqueous HF and a second contact wherein the ammonium ion-treated ferrierite is contacted with aqueous HF and the aqueous HF-treated ferrierite is contacted with the ammonium ion.

2. The process of claim 1 wherein the said catalyst is selective toward cracking normal paraffins.

3. The process of claim 1 wherein the α value of the said catalyst is substantially in excess of 200.

4. The process of claim 1 wherein the said catalyst is selective toward cracking normal paraffins and controlled amounts of isoparaffins.

5. The process of claim 1 wherein the ferrierite is first contacted with the ammonium ion.

6. The process of claim 1 wherein the ferrierite is first contacted with aqueous HF.

7. The process of claim 1 wherein the hydrocarbon is 2,3-dimethylbutane.

8. The process of claim 1 wherein the hydrocarbon is 3-methylpentane.

* * * * *